United States Patent [19]

Patarin et al.

[11] Patent Number: 5,013,537

[45] Date of Patent: May 7, 1991

[54] PROCESS FOR THE SYNTHESIS OF ZEOLITES OF THE FERRISILICATE TYPE, PRODUCTS SO OBTAINED

[75] Inventors: Joël Patarin; Jean-Louis Guth, both of Mulhouse; Henri Kessler, Wittenheim; Gisèle Coudurier, Meyzieu; Francis Raatz, Rueil Malmaison, all of France

[73] Assignee: Institut Francais du Petrole, Rueil-Malmaison, France

[21] Appl. No.: 437,308

[22] Filed: Nov. 17, 1989

Related U.S. Application Data

[63] Continuation of Ser. No. 133,842, Dec. 16, 1987, abandoned.

[30] Foreign Application Priority Data

Dec. 16, 1986 [FR] France ................................ 86 17711

[51] Int. Cl.$^5$ .............................................. C01B 33/34
[52] U.S. Cl. .................................... 423/328; 423/326; 502/66; 502/77; 208/134; 208/115; 208/119; 585/709; 585/721; 585/733; 585/408
[58] Field of Search ............... 423/328, 326, 329, 330, 423/594; 502/77, 85, 66; 208/134, 115, 119; 585/709, 721, 733, 408

[56] References Cited

U.S. PATENT DOCUMENTS

| | | |
|---|---|---|
| 3,839,539 | 10/1974 | Elliott . |
| 4,046,859 | 9/1977 | Plank et al. . |
| 4,073,865 | 2/1978 | Flanigen et al. ................... 423/330 |
| 4,238,318 | 12/1980 | Kouwenhoven et al. .......... 423/326 |
| 4,269,813 | 5/1981 | Klotz . |
| 4,285,919 | 8/1981 | Klotz et al. . |
| 4,376,757 | 3/1983 | Hinnenkamp et al. ............. 423/328 |
| 4,401,637 | 8/1983 | Marosi et al. ...................... 423/329 |
| 4,456,582 | 6/1984 | Marosi et al. ...................... 423/328 |
| 4,503,023 | 3/1985 | Breck et al. ........................ 502/85 |
| 4,551,321 | 11/1985 | Marosi et al. ...................... 423/329 |
| 4,650,654 | 3/1987 | Arika et al. . |
| 4,656,016 | 4/1987 | Tarramasso . |
| 4,678,766 | 7/1987 | Rosinski ............................. 502/85 |

FOREIGN PATENT DOCUMENTS

| | | |
|---|---|---|
| 0049386 | 9/1981 | European Pat. Off. . |
| 0055529 | 7/1982 | European Pat. Off. . |
| 0065401 | 12/1982 | European Pat. Off. ............. 423/328 |
| 2567868 | 1/1986 | France . |
| 59-73425 | 4/1984 | Japan .................................. 423/328 |

OTHER PUBLICATIONS

Guth et al., "New Route to Pentasil-Type Zeolites Using a Non Alkaline Medium in the Presence of Fluoride Ions," Aug. 1986, pp. 121-128.

Y. Murakami et al., eds. New Developments in Zeolite Science and Technology, Proc. of the 7th Int'l. Zeolite Conf., Tokyo, Namba, "Shape Selective Cracking of Octane in the Presence of Another Hydrocarbon on HASM-5," pp. 661, 663.

Post et al., "An Infrared and Catalytic Study of Isomorphous Substitution in Pentasil Zeolites," 1989, pp. 362, 368, 371.

D. Olston et al., Proceedings of the Sixth Int'l. Zeolite Conf., Reno, 7-83, Haag, "Acid Catalysts with Medium Pore Zeolites," pp. 466, 472.

*Primary Examiner*—W. J. Shine
*Assistant Examiner*—R. Bruce Breneman
*Attorney, Agent, or Firm*—Millen, White & Zelano

[57] ABSTRACT

The invention relates to a novel process for the synthesis of zeolites of the ferrisilicate type called ferrizeosilites, to the products obtained by this process as well as their uses. Ferrizeosilite according to the invention is characterized by (a) a chemical formula close to the following:

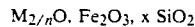

$M_{2/n}O \cdot Fe_2O_3, x\ SiO_2$ where
M represents a proton and/or a metal cation
n is the valence of said cation
x is a number between 40 and 1000

(b) an x-ray diffraction diagram, and (c) a fluorine content between about 0.01% and 16% by weight. Uses are in processes for the conversion of methanol into hydrocarbons, alkylation of toluene with methanol and catalytic cracking of hydrocarbons.

18 Claims, No Drawings

PROCESS FOR THE SYNTHESIS OF ZEOLITES OF THE FERRISILICATE TYPE, PRODUCTS SO OBTAINED

This application is a continuation of application Ser. No. 07/133,842, filed Dec. 16, 1987, now abandoned.

BACKGROUND OF THE INVENTION

The present invention relates to a novel process for the synthesis of zeolites of the ferrisilicate type called ferrizeosilites, the products obtained by this process.

The zeolites are crystalline tectosilicates. Their three dimensional structure is constructed by an assembly of $TO_4$ tetrahedra, placing their tops in common, two different tetrahedra only having one oxygen in common. In zeolites of the aluminosilicate type, which are the most common, T represents tetravalent silicon as well as trivalent aluminum. The cavities and channels of molecular dimensions, of the covalent framework receive the cations compensating for the charge deficit associated with the presence of the trivalent aluminum in the tetrahedra. Some rare zeolites are also known wherein the silicon is replaced by tetravalent germanium. Similarly, trivalent elements like gallium and more rarely boron or divalent elements like beryllium may be substituted for the aluminum.

Generally, the composition of the zeolites may be represented by the crude formula $M_{2/n}O, Y_2O_3, xZO_2$ in the dehydrated and calcined state. Z and Y represent respectively the tetravalent and trivalent elements of the tetrahedra $TO_4$; M represents an electro-positive element of valency n, such as an alkali or alkaline-earth; x can vary from 2 to theoretically infinity in which case the zeolite is a silica.

Each type of zeolite has a distinct porous structure. The variation of the sizes and shapes of the pores from one type to another results in a change in the absorbance properties. Only molecules of certain sizes and shapes can enter the pores of a particular zeolite. The chemical composition with, in particular, the nature of the exchangeable compensation cations, is also an important factor taking part in the selectivity of the adsorption and especially the catalytic properties of these products.

Due to their particular characteristics (molecular sieves and cation exchangers, the zeolites are used both in adsorption and in catalysis. Among the uses in adsorption may be mentioned the purification of gases, the separation of hydrocarbons; in catalysis several important processes use zeolites as catalysts: catalytic cracking, hydrocracking, isomerisation etc.

Although numerous zeolites of the aluminosilicate type exist in nature, research for products having novel properties has led in the course of recent years to the synthesis of a great variety of these aluminosilicates with a zeolitic structure.

In addition, several patents claim the partial or even total substitution of the aluminum atoms of the crystalline framework by elements of oxidation degree III, (boron, gallium, iron . . . ). After replacement of the compensation cations by protons by techniques known in the prior art, acid solids are obtained in which the strength of the sites will vary according to the nature of the one or more elements (boron, gallium, iron . . . ) which have been substituted for silicon within the framework. Thus, for example, zeolites containing silicon and iron in their crystalline framework have acid properties different from those of zeolites of the same crystalline structure containing silicon and aluminum in their framework.

By way of example, in the case of substitution of Al by FeIII, see German patent DE No. 2831611, European patents EP 813532, 884422 and 115031.

In addition, the prior art may be illustrated by the patents EP-A-160,136, EP-A-30,751 and CA-A-1.197.498.

Generally, the zeolites are prepared by hydrothermal crystallization of reaction mixtures containing alkaline or alkaline-earth hydroxide sources, silica, and oxides or salts of elements like aluminum which can replace the silicon in the tetrahedra.

The addition to the reaction mixture of a generally organic structural member, such as an amine or a quaternary ammonium salt, is often necessary for the formation of said zeolite. The pH of the whole of the preparation is basic and generally higher than 10. It is acknowledged that the concentration of $OH^-$ ions facilitates the crystallization of the zeolite by ensuring the dissolution of the silica sources, and, possibly of amphoteric oxides like alumina, as well as the transfer of the soluble species thus obtained to the zeolite being formed.

This method of synthesis of the zeolites has numerous drawbacks particularly if it is desired to replace the aluminum by iron. In fact, in a basic medium, the majority of the zeolites synthesized are metastable and there is a risk of the appearance, in the course of the preparation, of more stable but undesired solid phases, as well as the precipitation of ferric hydroxide. This difficulty only increases when the amounts prepared increase, that is to say on the industrial scale.

Besides, these zeolites which are metastable in the basic reaction medium are only obtained from a high supersaturation of active species in the medium, which causes rapid nucleation and leads to zeolite crystals of small size, the average size of these crystals being in the range of a micrometer. The formation of crystals of larger size is hence difficult. In certain applications of ion exchange, adsorption or catalysis, it would be interesting to be able to work with crystals of large size which, for example, would permit the conditioning of the zeolites by agglomeration, with all the drawbacks that this brings, being avoided.

Numerous applications, in particular in acid catalysis, require zeolites in a protonized form and completely freed from their alkaline or alkaline-earth compensation cation introduced during the synthesis. It is possible here to arrive at this by repeated and long ion exchange processes with $NH_4^+$ cations followed by calcination to decompose them into $H^+$ cations. This ion exchange step could be eliminated if it were possible to replace entirely the alkali metal or alkaline-earth metal cations by $NH_4^+$ cations during the synthesis. Now, this is not possible when the pH substantially exceeds 10, $NH_4^+$ being converted under these conditions into $NH_3$. In addition, synthesis carried out at pH's where the $NH_4^+$ cation is stable are difficult and time consuming on account of the low solubility of the sources of silica at these low pH's.

GENERAL DESCRIPTION OF THE INVENTION

It is therefore an object of the invention to provide a synthetic crystalline zeolite of the ferrisilicate type called ferrizeolite belonging to the family of pentasils, a novel process of synthesising this zeolite wherein the above mentioned drawbacks are avoided and the applications of this novel type of solid.

More precisely the novel zeolite is characterized by:
(a) the following approximate chemical formula $$M_{2/n}O, Fe_2O_3, xSiO_2$$

where
M represents a proton resulting from the thermal decomposition of cations like for example $NH_4^+$ or tetrapropyl or tripropylammonium or tetrapropylphosphonium present alone or in admixture in the synthesis medium, and (or) a non-decomposable metal cation coming from the reaction medium like for example alkali and/or alkaline-earth cations or other metals specified below,
n is the valence of said cations
x is a number comprised between 40 and 1000,
(b) an X diffraction diagram shown in Table I of the description, and
(c) a fluorine content comprised between about 0.01 and 1.6% by weight.

The zeolite according to the invention can generally have at least one dimension of the crystals comprised between 0.1 and 200 micrometers (1 $\mu m = 10^{-6}$ m) and preferably comprised between 0.5 and 120 micrometers.

The ferrizeosilite of the present invention may generally possess a molar ratio $SiO_2/Fe_2O_3$ comprised between 40 and 1000 and preferably between 50 and 750.

The presence after calcination (conditions specified below) of fluorine in the ferrizeosilite, preferably between 0.02 and 1% by weight results in modifications of its acid properties. This fluorine may, if necessary, be eliminated by treatment in a $NH_4OH$ solution in an autoclave between 130° and 180° C.

In the case where metal cations, for example alkali metals or alkaline-earth metals would be introduced during the synthesis, these ions can be easily eliminated by conventional ion exchange operations to obtain an acid ferrizeosilite.

The invention also relates to catalysts comprising the above-described novel ferrizeosilite.

The ferrizeosilite may in fact be used alone or associated with a catalyst. In this case the catalyst contains about at least 0.1% and preferably at least 20% of ferrizeosilite according to the invention, the complement to 100% being constituted by another zeolite or by a matrix comprising compounds selected from the group formed by alumina, silica, magnesia, zirconia, titanium oxide, boron oxide, a clay and any other combination of at least two of these aforesaid compounds. If necessary the catalyst may comprise at least one hydrogenating or dehydrogenating function contributed by at least one metal selected preferably from among the groups $I_B$ and VIII or contributed by a metal sulfide selected from among the groups $VI_B$ and VIII.

The invention also relates to the process of preparation of ferrizeosilites of the ferrisilicate type of the family of pentasils, which consists of:
(a) Forming a reaction mixture in solution having a pH less than about 10 and comprising water, at least one source of silica, at least one source of ferric salt, at least one source of mobilizing agent containing fluoride ions, ($F^-$) and at least one source of templating agent which can provide organic cations, for example tetrapropylammonium ($TPA^+$), tetrapropylphosphonium ($TPP^+$) and tripropylammonium ($TriPA^+$), said mixture having a composition in terms of molar ratios:

| | |
|---|---|
| $SiO_2/Fe_2O_3$ | 5-2000 |
| $F^-/SiO_2$ | 0.04-4 |
| Organic cations/$SiO_2$ | 0.04-2 |
| $H_2O/SiO_2$ | 6-500 |

(b) Maintaining said mixture at a temperature at the most equal to 250° C. until a crystalline compound is obtained, and
(c) calcining said compound at a temperature higher than 400° C., for example between 450° and 900° C.

The sources of structurating agent which can provide organic cations are preferably tetrahydrocarbylammonium, trihydrocarbylammonium, tetrahydrocarbylphosphonium cations, hydrocarbyl being advantageously alkyl and preferably propyl.

Other templating or chelating agents may be used as recognized in the prior art, particularly compounds having amine, ketone, alcohol, or acid functions, for example, amino alcohols, amino acids, polyalcohols or tertiary amines.

The mixture may advantageously be heated in an autoclave lined internally with polytetrafluoroethylene (PTFE) between about 60° C. and 210° C. and preferably between 70° C. and 190° C. for a duration which can vary from 0.5 to 1100 hours according to the reaction temperature, until the production of a crystalline solid which is separated from the mother-liquors by filtration and which is then washed with distilled water.

Advantageously, it is possible to prepare the reaction mixture at a pH comprised between 2.5 and 10 and preferably between 4 and 8.

In a preferred embodiment of the preparation, the molar ratios of the constituents of the reaction mixture may be comprised in the ranges (expressed in molar ratios) as follows:

| | |
|---|---|
| $SiO_2/Fe_2O_3$ | 10-1000 |
| $F^-/SiO_2$ | 0.1-1.5 |
| Organic cation/$SiO_2$ | 0.08-1 |
| $H_2O/SiO_2$ | 15-350 |

It is possible to add to said reaction mixture at least one complementary salt in a molar ratio complementary salt/$SiO_2$ comprised generally between about 0.1 and 4 and preferably between 0.2 and 0.5 and/or at least one crystal germ of the zeolite formed according to the invention in a ratio by weight crystal/$SiO_2$ comprised generally between 0.01 and 0.1 and preferably between about 0.02 and 0.03, so that the morphology, the size of the crystals as well as the kinetics of the crystallisation reaction may be advantageously controlled.

Advantageously the zeolite crystals are calcined at a temperature comprised of between about 520° and 590° C. in a dry gaseous atmosphere like for example air or an inert gas, so as to decompose the templating agent present in the pores of the zeolite.

After the calcination step there may be introduced into the ferrizeosilite according to the invention, by ion exchange methods well known in the prior art, at least one element of the periodic table, whose cations may be prepared in an aqueous medium and selected from the family constituted by groups $II_A$, $III_A$, $IV_A$, $I_B$, $II_B$, $III_B$, $IV_B$, and VIII of the periodic classification of the elements. By way of example may be mentioned the alkali, alkaline-earth cations, rare earth cations, $Fe^{II}$, $Fe^{III}$, $Co^{II}$, $Co^{III}$, $Ni^{II}$, $Cu^{II}$, $Zn^{II}$, $Ag^{I}$, $Pt^{II}$ etc.

The novel process applies to the preparation of novel zeolites of the family of pentasils and related to zeolites of the MF1 type, whilst being distinguished from the latter by particularities of the x-ray diffraction diagrams and of the chemical compositions.

Applicant has in fact discovered that the different disadvantages associated with the methods of preparing zeolites of the ferrisilicate type in a basic medium disappear when the syntheses are carried out in aqueous media with a pH generally less than 10 and containing fluoride ions. Thus, cations derived from alkali or alkaline-earth metals may be replaced by $NH_4^+$ cations with all the advantages derived from the use of the latter cations. The solubilisation of sources of silica and of iron is ensured by the fluoride ions which constitute the mobilising agent, and which thus replace the hydroxyl ions of the basic media. Under these conditions it is possible to obtain zeolite crystals of the ferrisilicate type having molar ratios $SiO_2/Fe_2O_3$ generally comprised between about 40 and 1000. Said crystals have sizes which can be controlled from different parameters of synthesis (concentration of reagents, stirring, temperature, duration), and the sizes of said crystals can vary between 0.05 micrometers and 500 micrometers.

The sizes of the crystals given above have been measured by means of a high resolution electron microscope. The catalyst, intended to be observed by transmission electron microscopy is ground in an agate mortar, then suspended in ethanol by ultra sound. A drop of the suspension is then deposited on a copper grid covered with a thin film of porous carbon. After brief drying, the sample is observed by the so-called bright field technique.

Advantageously operations are carried out in a medium under stirring, which permits the reaction time to be considerably reduced.

The pH of the reaction medium, less than 10, may be obtained either directly from one or several of the reagents employed, or by the addition of an acid, of a base, of an acid salt, of a basic salt or of a complementary buffer.

Numerous sources of silica may be used. Mention may be made of silicas in the form of hydrogels, aerogels, colloidal suspensions as well as silicas resulting from the precipitation of soluble silicate solutions or from the hydrolysis of silicic esters like tetraethyl ester of orthosilicic acid $Si(OC_2H_5)_4$ or of complexes like sodium fluorosilicate $Na_2SiF_6$ or ammonium fluorosilicate $(NH_4)_2SiF_6$.

Among the ferric salts used, ferric chloride, hydrated or not, $FeCl_3 \cdot 6HO$ or $FeCl_3$, the nonahydrated ferric nitrate $Fe(NO_3)_3 \cdot 9H_2O$, the pentahydrated ferric sulphate as well as the ferric perchlorate, are preferably selected. In addition, instead of starting from separate sources of silica and a ferric salt it is also possible to take sources wherein the two elements are combined such as, for example, a freshly precipitated ferrisilicate gel.

The fluoride $F^-$ anions can generally be introduced in the form of salts of said templating agents or of ammonium or of alkali metals such as for example, NaF, $NH_4F$, $NH_4HF_2$, TriPA-F, TPA-F, TPP-F, or in the form of hydrolyzable compounds which can release fluoride anions into the water such as silicon fluoride $SiF_4$ or ammonium fluorosilicate $(NH_4)_2 SiF_6$ or sodium fluorosilicate $Na_2SiF_6$.

The cations $TPA^+$, $TPP^+$ or $TriPA^+$, which are templating agents, are added preferably in the form of their salts, for example, bromides, fluorides, etc, but it is possible also to add the corresponding amines (tripropylamine for example), which are then salified with acid, hydrofluoric, for example.

The acids or acid salts, the bases or basic salts added if necessary as a complement to bring the pH of the medium to the desired value maybe selected from among the usual acids, like for example, HF, HCl, $HNO_3$ $H_2SO_4$, $CH_3COOH$ or the acid salts like for example $NH_4HF_2$, $KHF_2$, $NaHSO_4$, $KHSO_4$, the usual basis like for example $NaHCO_3$, $Na_2CO_3$, $CH_3COONa$, $Na_2S$, NaHS or the buffer mixtures like for example ($CH_3COOH$, $CH_3COONa$) or ($NH_4Cl$, $NH_4OH$).

The morphology, the size and the kinetics of formation of the zeolite crystals obtained by the process of the invention may be modified by the introduction into the reaction medium of at least one complementary salt selected from the group of chlorides of alkaline metals, sulphates of alkaline metals and ammonium chloride. Advantageously sodium chloride, potassium chloride and/or ammonium chloride are used as well as sodium sulphate. The morphology, size and kinetics of formation of the zeolite crystals obtained according to the process of the invention may also be modified by the introduction into the reaction medium of germs constituted by crystals (ground or not) belonging to the family of zeolites forming the subject of the present application.

The development of the composition in the midst of ferrizeosilite crystals can be advantageously modulated, on the one hand, according to the silica sources and the ferric salt used and on the other hand according to the silica/iron ratios involved.

For ratios $SiO_2/Fe_2O_3 > 80$, when starting from separate sources of silica and of ferric salt, the crystals obtained show an intracrystalline heterogeneity with a core particularly rich in iron (low ratio Si/Fe) and an envelope rich in silica (high Si/Fe ratio). The formation of a ferrisilicate gel enables on the other hand the obtaining of ferrizeosilite crystals whose composition is completely homogeneous in the group of crystals.

For certain applications it can be established to be advantageous to prepare ferrizeosilites according to the invention having a core rich in iron hence an outer surface constituted almost entirely of silica. Under these conditions the outer surface of the crystals do not contain active sites (iron atoms) which results in an improvement in the selectivity in the form of the catalysts since the reactions can only occur in the microporous lattice.

The identification of the ferrizeolites obtained by the process is done conveniently from their x-ray diffraction diagram. This diffraction diagram can be obtained by means of a diffractometer by using with the conventional power method with $K\alpha$ radiation from copper. An internal standard enables the precise determination of the values of the angles $2\theta$ associated with the diffraction peaks. The different interreticular distances $d_{hkl}$, characteristic of the sample, are calculated from the BRAGG relationship. The estimation of the error of measurement $\Delta$ $(d_{hkl})$ on $d_{hkl}$ is calculated, as a function of the absolute error $\Delta$ $(2\theta)$ associated with the measurement of $2\theta$ by the BRAGG relationship. In the presence of an internal standard, this error is minimised and taken currently as equal to $\pm 0.05°$. The relative intensity I/Io associated with each value of $d_{hkl}$ is estimated from the height of the corresponding diffraction peak. A scale of symbols is often used to characterise this intensity: FF=very strong, F=strong, mF=moderate to strong, m=moderate, mf=moderate to weak, f=weak, ff=very weak.

The table below, represents the x-ray diffraction diagram characteristic of zeolites of the ferrisilicate type obtained according to the invention calcined at 550° C. In the column of the $d_{hkl}$ are shown the extreme values that the different reticular equi-distances $d_{hkl}$ can assume. The column "o" corresponds to a ferrizeolite crystallising in the orthorhombic system (Si/Fe low), the column "m" corresponds to a ferrizeolite crystallising in the monoclinic system (Si/Fe high). The variations observed are essentially connected with the nature of the compensation cations and with the ratio Si/Fe of the zeolite. Each of these values must be associated with the error of measurement $\Delta$ ($d_{hkl}$) comprised between $\pm 0.07$ and $\pm 0.002$ according to the value of $2\theta$.

The invention also relates to the use of a zeolite according to the invention alone or associated with a matrix both in adsorption and in catalysis.

In fact the ferrizeolites prepared according to the invention are selective adsorbants; their adsorbant properties are very close to those of zeolites of the aluminosilicate type.

Besides, the ferrizeolites may be used as catalysts or catalyst supports, pure or in admixture, for very specific transformations of various organic compounds. It is possible to mention by way of example, alkylation, dismutation and transalkylation of aromatics, oligomerization of olefins, conversion of alcohols like methanol into hydrocarbons, the conversion of propene into hydrocarbons with a high content of aromatics, the improvement of the cold behavior of gas oils and catalytic cracking.

Catalytic cracking appears as one of the important applications of ferrizeosilites according to the invention. For this application it is preferred to use ferrizeosilites in admixture with a zeolithic cracking catalyst, in the proportion of 0.1 to 10% by weight, preferably 0.5 to 5% by weight, of ferrizeosilite in that the mixture, the complement to 100% being constituted by the zeolithic catalyst and a matrix selected from among those already known in the prior art. Preferably the cracking catalyst contains a Y zeolite, for example the so called ultrastable stabilized form (USY), the dealuminized form Y (overall molar ratio Si/Al comprised between 3.5 and 50), the ReY form (exchanged at least in part with rare earth cations) containing from 0.05 to 20% by weight of rare earths in the form of oxide $Re_2O_3$.

The moderate acidity of these ferrizeolites, demonstrated by programmed $NH_3$ thermodesorption, enables avoiding too high a formation of coke, and also reduction of the cracking reactions, this having the consequence of ensuring a longer life for the catalyst.

TABLE I

| $d_{hkl}$ | | | $d_{hkl}$ | | |
|---|---|---|---|---|---|
| o | m | I | o | m | I |
| 11.14 | 11.10 | FF | 3.44 | 3.45 | mf |
| 9.99 | 9.92 | FF | | 3.43 | mf |
| 9.76 | 9.76 | mF | 3.38 | 3.37 | ff |
| 9.02 | 9.00 | f | 3.353 | 3.353 | mF |
| 8.08 | 8.03 | ff | 3.321 | 3.313 | mF |
| 7.45 | 7.42 | f | 3.247 | 3.254 | f |
| 7.10 | 7.06 | ff | 3.133 | 3.131 | ff |
| 6.72 | 6.69 | f | | 3.058 | m |
| 6.38 | 6.36 | m | 3.052 | | m a mf |
| 6.03 | 5.99 | mF | | 3.036 | m |
| 5.95 | 5.93 | mF | 2.990 | 2.986 | m |
| | 5.72 | m | | 2.955 | mf |
| 5.70 | | m | | 2.942 | mf |
| | 5.68 | m | | 2.921 | ff |
| 5.57 | 5.57 | m | 2.866 | 2.864 | ff |
| 5.38 | 5.38 | ff | 2.783 | 2.782 | ff |
| | 5.33 | ff | 2.733 | 2.733 | f |
| 5.15 | 5.13 | ff | 2.685 | 2.679 | ff |
| 5.04 | 5.03 | m | 2.662 | 2.660 | ff |
| 4.99 | 4.97 | mF | | 2.613 | f |
| 4.88 | 4.88 | ff | 2.605 | | f |
| 4.62 | 4.62 | mf | | 2.589 | f |
| 4.46 | 4.40 | ff | 2.510 | 2.513 | f |
| 4.37 | 4.36 | mf | 2.488 | 2.484 | mf |
| 4.27 | 4.26 | m | 2.455 | 2.457 | ff |
| 4.09 | 4.08 | ff | 2.441 | 2.441 | ff |
| 4.01 | 4.01 | f | 2.416 | 2.413 | f |
| 3.86 | 3.85 | FF | 2.395 | 2.392 | f |
| 3.82 | 3.82 | FF | 2.325 | 2.324 | ff |
| | 3.80 | FF | 2.275 | 2.274 | ff |
| | 3.76 | F | 2.203 | 2.202 | ff |
| 3.75 | 3.74 | F | 2.011 | 2.011 | m a mf |
| 3.72 | 3.71 | F | 1.992 | 1.987 | mF |
| | 3.66 | mF | | | |
| 3.65 | 3.62 | mF | | | |
| 3.56 | 3.56 | ff | | | |
| 3.49 | 3.49 | f | | | |

"o" Orthorhombic ferrizeolite; "m" monoclinic ferrizeolite

The following examples are intended to illustrate the invention, without limiting the scope thereof.

EXAMPLE 1

Preparation of a ferrizeosilite of molar ratio $SiO_2/Fe_2O_3$ equal to 84

A solution containing 0.376 g of hexahydrated ferric chloride, 1.185 g of tetrapropylammonium bromide (TPABr) and 1.030 g of ammonium fluoride in 100 g of water is prepared. This solution is mixed with 3.343 g of powdered silica, obtained by pyrohydrolysis of silicon tetrachloride and marketed by the Degussa company under the name "Aerosil", the latter contains 3% by weight of water approximately. In addition, the content by weight of aluminum is less than 0.002%. The molar composition of the mixture brought to 1 mole of silica is as follows: 1 $SiO_2$; 0.025 $FeCl_3 6H_2O$; 0.08 TPABr; 0.5 $NH_4F$; 100 $H_2O$.

The mixture (pH=6) is heated for 15 days at 170° C. in an autoclave containing a bottle of 120 $cm^3$ of polytetrafluoroethylene; the final pH was 6. The solid obtained after filtration and washing with twice-distilled water weighed 3.62 g.

The size of the crystals of prismatic shape was 60×36 micrometers. The loss in weight observed after calcination of the zeolite at 550° C. under a mixture of 20% air in 80% nitrogen for 9 hours, was 14.2%. The calcined sample, placed in a humidifier (water/$NH_4Cl$), takes up 5.8% by weight of water.

X-ray diffraction analysis of the rehydrated calcined product shows that it is a ferrizeolite characterized by the diffraction diagram of Table I. Chemical analysis of this ferrizeosilite gives a value of iron of 2.05% and of fluorine of 0.06% by weight, and a molar ratio $SiO_2/Fe_2O_3$, equal to 84.

EXAMPLE 2

Preparation of a ferrizeosilite according to the invention from a templating agent other than that used in Example 1

This example illustrates the possibility of using as a templating agent tripropylamine in place of tetrapropylammonium bromide. The molar composition of the reaction mixture in this case was as follows: 1 $SiO_2$ (Aerosil); 0.05 $FeCl_3$; 1 tripropylamine; 1 HF; 50 $H_2O$. Molar fraction involved: 6%.

The tripropylamine is previously salified with hydrofluoric acid. In addition, 0.072 g of crystals of a previously synthesised ferrizeosilite, were also added to the whole of the preparation. The conditions of heating in an autoclave, and The conditions of heating in an autoclave, and the values of pH are respectively: duration: 12 days, temperature: 170° C., initial pH: 5, final pH: 4.

The solid obtained after washing and filtration was treated with sodium dithionite in order to extract all traces of ferric oxide or oxy-hydroxide present in this particular case. The prismatic crystals thus obtained have a size close to 7.5×2 micrometers. Chemical analysis gives contents by weight of iron and of fluorine of 1.96 and of 0.2% respectively. The diffraction diagram of the product calcined at 550° C. under the same conditions as those of Example 1 is in accordance with that of Table I. The molar ratio $SiO_2/Fe_2O_3$ measured by chemical analysis was equal to 78.

EXAMPLE 3

Preparation of a ferrizeosilite according to the invention from another source of fluoride ions than that used in Example 1

In this preparation there were used as the source of fluoride agent, sodium fluoride in place of ammonium fluoride, the sources of silica and of iron being always the same as in Example 1. The molar composition of the mixture thus employed was: 1 $SiO_2$: 0.025 $FeCl_3 6H_2O$; 0.5 NaF; 100 $H_2O$; 0.08 TPABr. 5.5% of the molar proportions were involved. The reaction mixture was brought, in an autoclave, to a temperature of 170° C. for 16 days (the initial pH was equal to 6.1).

The solid thus obtained was placed in an ultrasonic tank in order to separate the traces of residual gel from the crystals.

After sonification, washing and filtration, 2.5 g of product was recovered whose chemical composition by weight was as follows: % Si=38.5; % Fe=1.92; % $TPA^+$=10.9; % $F^-$=0.3; % $Na^+$=0.03 (molar ratio $SiO_2/Fe_2O_3$=80). The prismatic crystals of this ferrizeosilite, were twinned and have a size close to 60×40 micrometers.

The product calcined at 550° C. under the same conditions as those of Example 1, had an x-ray diffraction diagram similar to that of Table 1. After calcination the fluorine content was equal to 0.10% by weight.

EXAMPLE 4

Preparation of a ferrizeosilite according to the invention of molar ratio $SiO_2/Al_2O_3$ equal to 46

A mixture having the following molar composition was prepared: 1 $SiO_2$ (Aerosil); 0.05 $FeCl_3$; 0.25 TPABr; 0.5 $NH_4F$; 33 $H_2O$; by using 8% of the molar amounts indicated.

The mixture (pH=6) was heated for 7 days at 190° C. in the same type of autoclave as that of the preceding examples; the final pH was 6. The chemical analysis of the solid obtained after sonification (4 g) leads to a molar ratio $SiO_2/Fe_2O_3$, equal to 46, the fluorine content was 0.14% by weight. The x-ray diffraction diagram of the product calcined in air at the temperature of 550° C. for 9 hours in pure air corresponds to that of Table 1.

The twinned prismatic crystals have an average size of 100×50 micrometers.

EXAMPLE 5

Preparation of a ferrizeosilite according to the invention from a source of iron and of silica other than those used in Example 1.

This example illustrates the possibility of starting from a ferrisilicate gel as a source of silicon and of iron.

A gel of the composition: 1 $SiO_2$; 0.025 $FeCl_3$ is prepared by the addition, with stirring, of a ferric chloride solution to a sodium silicate solution. Final pH of the mixture (6.5) is obtained by the addition of a concentrated nitric acid solution. In order to remove all traces of sodium, the hydrogel is exchanged with a concentrated solution of ammonium nitrate. After several washings, the gel is then dried at 80° C. for 24 hours.

Chemical analysis of the latter leads to a molar ratio Si/Fe of 44. After homogenization of this powder, a mixture is produced whose molar composition is as follows: 1 Si; 0.023 Fe; 0.08 TPABr; 0.5 $NH_4F$; 40 $H_2O$. 10% of the molar amounts indicated are engaged in an autoclave similar to those described in the preceding examples and then the whole is heated to 170° C. for 15 days. The solid so obtained (m=4.9) is filtered and washed with distilled water. After drying and calcination at 550° C. in air for 3 hours, a ferrizeosilite is obtained of which the X diffraction diagram is in accordance with Table I. The size of the crystals is close to 30×11 micrometers. The molar ratio $SiO_2/Fe_2O_3$ determined by chemical analysis is equal to 80, and the fluorine content after calcination is about 0.08% by weight.

EXAMPLE 6

Preparation of a ferrizeosilite of molar ratio $SiO_2/Fe_2O_3$ equal to 196 from a silicate gel and leading to a homogeneous distribution of the iron with the crystals In this example a ferrisilicate gel is also prepared with, as source of silica, the tetraethyl ester of orthosilicic acid $Si(OC_2H_5)_4$.

25 $cm^3$ of $Si(OC_2H_5)_4$, 0.3 g of $FeCl_3 6H_2O$ and 50 $cm^3$ of H O are brought to reflux for 3 hours. After precipitation of the ferrisilicate gel, the latter is dried at 80° C. for 2 days, then finally ground. Chemical analysis of the latter results in the following percentages by weight: % Si=39; % Fe=0.75.

A mixture is then made up whose molar composition is as follows: 1 Si; 0.01 Fe; 0.08 TPABr; 0.5 $NH_4F$; 100 $H_2O$. The molar fraction engaged is 5%. The initial pH is 6. The whole placed in an autoclave is brought to 170° C. for 15 days. After the reaction (final pH=6.5), 3.52 g of a ferrizeosilite is obtained whose chemical analysis results in molar ratio $SiO_2/Fe_2O_3$ of 196. Analysis with the electron microprobe on previously polished samples, establishes a homogeneous distribution of the iron within the ferrizeosilite crystals. The size of the crystals thus obtained is close to 30×20 micrometers. The x-ray diffraction diagram of this ferrizeosilite calcined in air at 550° C. for 9 hours, corresponds to that of Table 1. The fluorine content after calcination is equal to 0.03% by weight.

EXAMPLE 7

Preparation of the ferrizeosilite according to the invention of molar ratio $SiO_2/Fe_2O_3$ equal to 155 from separate sources of silica and of iron, leading to a non-homogeneous distribution of the iron within the crystals The reagents used in this example are the same as those used in Example 1. The molar composition of the mixture so employed is: $1SiO_2$; $0.013FeCl_3$, $6H_2O$; $0.5NH_4F$; $100H_2O$; $0.08TPABr$. Initial pH=6. 5.5% of the molar proportions are engaged.

The reaction mixture, placed in the same type of autoclave as that of the preceding example is brought to a temperature of 170° C. for 15 days. After the reaction (final pH=6) 3.6 g of a ferrizeosilite is obtained whose chemical analysis leads to a molar ratio $SiO_2/Fe_2O_3$ of 155.

Study of this compound with the electron microprobe establishes an intracrystalline heterogeneity. The crystals are constituted by a core rich in iron of which the molar ratio $SiO_2/Fe_2O_3$ is close to 80 and an envelope rich in silicon with a molar ratio $SiO_2/Fe_2O_3$ close to 2000.

The size of the crystals obtained is close to $50 \times 40$ micrometers. The x-ray diffraction diagram of this ferrizeosilite calcined in air at 550° C. for 9 h and rehydrated corresponds to that of Table I. After calcination the fluorine content is equal to 0.2% by weight.

EXAMPLE 8

Preparation of the ferrizeosilite according to the invention in a medium under stirring This example demonstrates the possibility of operating in a stirred medium and thus of considerably reducing the reaction time. The following reaction mixture is prepared: 1 SiO (Aerosil); $0.015$ $FeCl_36H_2O$; 0.2 TPABr; 0.4 $NH_4F$; 100 $H_2O$. The molar fraction engaged is 5.5%. Initial pH is 6. The whole placed in the same type of autoclave as previously is brought to temperature in a stove equipped with a mechanical stirring system ensuring the total inversion of the autoclaves and whose speed of rotation can be modulated. The characteristics of the reaction for this example were the following: temperature=170° C.; speed of rotation=17 rpm; duration: 3 days.

After the reaction (final pH=6), 3.8 g of a ferrizeosilite is obtained whose crystals have an average size of $40 \times 20$ micrometers. Chemical analysis of this ferrizeosilite leads to a molar ratio $SiO_2/Fe_2O_3$ equal to 140.

The x-ray diffraction diagram of the ferrizeosilite previously calcined in air at 550° C. for 9 hours, corresponds to that of Table I. The fluorine content determined after calcination is equal to 0.032% by weight.

EXAMPLE 9

Preparation of ferrizeosilite according to the invention at temperatures below 100° C.

This example illustrates the possibility of carrying out synthesis at a temperature below 100° C., the addition of seeds enabling the duration of crystallisation to be reduced.

A mixture is formed whose molar composition is as follows: 1 $SiO_2$; 0.055 $FeCl_3$; 0.25 TPABr; 0.5 $NH_4F$; 100 $H_2O$. The silica source used was the same as in the preceding example. The reaction mixture contained also 1% by weight, with respect to the amount of silica engaged, of crystals of a finely ground ferrizeosilite. The initial pH was 6.2. The whole was placed in polypropylene bottle and brought to a temperature of 80° C. for 48 days. After several decantations, washings and filtrations 53 g of ferrizeosilite is obtained by which the x-diffraction diagram is in accordance with that of Table 1. The solid is then calcined at 550° C. under the same conditions as those of Example 1. Chemical analysis reveals a ratio $SiO_2/Fe_2O_3$ equal to 72 and fluorine content of 0.09% by weight.

Adsorption tests of n-hexane and of trimethylpentane were carried out on this sample. For a temperature of 20° C. and under a relative pressure of the adsorbate $P/Po=0.1$; the quantities absorbed were respectively 12.1% and 8.7% by weight. These characteristics are substantially similar to those of a zeolite of alumino silicate type.

EXAMPLE 10 (comparative)

Importance of the presence of fluoride ions in the synthesis medium

So as to determine to what extent the presence of fluoride ions in the reaction medium is important for the synthesis of ferrizeosilite, the following tests were carried out:

Test 1: a synthesis was carried out under the same conditions as those of Example 1. The only difference consisted of not adding ammonium fluoride.

Test 2: a synthesis was carried out under the same conditions as those of Example 2. The only difference consisted in that hydrofluoric acid was not added.

In the two cases, test 1 bis (heating to 170° C. for 15 days, see Example 1) and test 2 bis (heating to 170° C. for 12 days) an amorphous solid was obtained, no trace of ferrizeosilite being detected in the solid phase collected.

Test 1 bis and 2 bis were recommenced by varying the reaction time from 1 day to 30 days; in no case, was ferrizeosilite formed.

EXAMPLE 11

Use in the conversion of methanol of ferrizeosilite according to the invention

The catalytic properties of the ferrizeosilite obtained in Example 9 was studied with regard to two reactions which were the conversion of methanol into hydrocarbons and the alkylation of toluene into xylenes. Generally, the operational method was as follows. In a reactor 10 g of ferrizeosilite prepared according to Example 9 was placed and was calcined and activated in a flow of nitrogen for 16 hours at 400° C. According to the reaction studied, there was passed either pure methanol, or a mixture of methanol and toluene (the molar ratio toluene/methanol=3.96) over the catalyst.

Analysis of the effluent emerging from the reactor was performed for different reaction times by gas phase chromatography.

The reaction temperatures as well as the hourly spatial velocities (reagent weight per catalyst weight and per hour) for the two reactions were respectively 370° C.; 4.3 hours$^{-1}$ (conversion of methanol) and 400° C.; 6.1 hours$^{-1}$ (alkylation of toluene).

In Table II have been reported the results obtained in the conversion of methanol into hydrocarbons with the ferrizeosilite of the present invention and a zeolite of structure MFI of ratio Si/Fe=25 prepared in a conventional medium (basic) according to the techniques of the prior art, described in German patent DE No. 2831611, European patents EP 813532, EP 884422 and EP 115031.

In Table III are reported the results obtained for the alkylation of toluene with methanol for the ferrizeosilite of the present invention and a zeolite of structure MF1 of ratio Si/Fe=29 prepared in a conventional medium (basic) according to the techniques of the prior art, described in the above patents.

TABLE II
CONVERSION OF METHANOL AND COMPOSITION OF PRODUCTS

| FERRIZEOSILITE ACCORDING TO THE INVENTION | | | | |
|---|---|---|---|---|
| Time (min) | 30 | 240 | 660 | 2010 |
| % methanol | 24 | 29,5 | 43 | 47 |
| % dimethylether | 20 | 24,5 | 46 | 42 |
| % hydrocarbons | 56 | 46 | 11 | 11 |
| % $C_1$, $C_2$, $C_3$ | 43 | 43 | 41 | 30 |
| % $C_4 \rightarrow C_{10}$ | 57 | 57 | 59 | 70 |
| ZSM5 WITH IRON | | | | |
| % methanol | 30 | 39 | 50 | 60 |
| % dimethylether | 25 | 30 | 35 | 38 |
| % hydrocarbons | 45 | 31 | 15 | 2 |
| % $C_1$, $C_2$, $C_3$ | 48 | 46 | 40 | 31 |
| % $C_4 \rightarrow C_{10}$ | 52 | 54 | 60 | 69 |

TABLE III
ALKYLATION OF TOLUENE

| FERRIZEOSILITE ACCORDING TO THE INVENTION | | | | |
|---|---|---|---|---|
| Time (min) | 30 | 195 | 280 | 325 |
| % toluene conversion* | 12.7 | 11.5 | 11.0 | 10.7 |
| % methanol conversion | 99.6 | 99.3 | 99.5 | 99.4 |
| % selectivity | | | | |
| paraxylene | 62.5 | 59.2 | 59.9 | 56.6 |
| metaxylene | 16.8 | 17.4 | 17.1 | 18.0 |
| orthoxylene | 20.7 | 23.4 | 23.0 | 25.4 |
| % xylenes/toluene converted | 91 | 90 | 92 | 92 |
| ZSM5 WITH IRON | | | | |
| % toluene conversion | 10.0 | 9.8 | 9.0 | 8.7 |
| % methanol conversion | 98.0 | 98.6 | 98.3 | 98.3 |
| % selectivity | | | | |
| paraxylene | 60.0 | 59.0 | 55.1 | 53.3 |
| metaxylene | 19.1 | 18.8 | 22.0 | 21.7 |
| orthoxylene | 20.9 | 22.2 | 22.9 | 25.0 |
| % xylenes/toluene converted | 88.8 | 89.0 | 89.1 | 89.4 |

*possible maximum conversion of toluene: 25.35% (molar ratio toluene/methanol = 3.96).

Table III shows that the ferrizeosilites prepared according to the invention have better performances both on the level of selectivity and activity than the iron zeolites of structure MF1 prepared in conventional media.

EXAMPLE 12

Application in the oligomerisation of olefines of the ferrizeosilites according to the invention In this example it is shown that the ferrizeolites perform well in the oligomerisation of olefins and that the fluorine contained in the solid after calcination at 550° C. enables the catalyst performance to be improved.

As a starting material there was used the ferrizeosilite of Example 1 whose molar ratio $SiO_2/Fe_2O_3$ is equal to 84 and whose fluorine content after calcination at 550° C. (described in Example 1) was 0.06% by weight. This ferrizeosilite was given the reference FZ1. FZ1 was subjected to defluoration treatment by treating it in a solution of $NH_4OH$ 0.25N at 160° C. in an autoclave. On emerging from this treatment the solid was subjected to calcination at 550° C. in air for 3 hours; it was then given the reference number FZ2. The fluorine content of FZ2 was very much less than that of FZ1, it was less than 0.008% by weight.

The ferrizeosilites FZ1 and FZ2 were tested in the oligomerization of propene. For this 20 g of ferrizeosilite were placed in the center of a reactor of 130 cm³ capacity. The catalyst was arranged between 2 beds of alpha alumina beads inert with respect to the oligomerisation reaction. Propene was then injected under the following conditions:
temperature
pressure:
hourly flow rate of propene: 1 kg/1 kg of catalyst
Under these operational conditions, the transformation level of the propene was 83% for FZ1 and 68% for FZ2. The liquid product withdrawn after separation of the unconverted propene, had the following characteristics for FZ1 and FZ2.

| | FZ1 | FZ2 |
|---|---|---|
| density at 20° C. | 0.780 | 0.762 |
| bromine index | 80 | 93 |
| ASTM distillation | | |
| Initial point: °C. | 75° C. | 54° C. |
| 10% vol.: | 138° C. | 118° C. |
| 30% vol.: | 160° C. | 142° C. |
| 50% vol.: | 201° C. | 186° C. |
| 70% vol.: | 242° C. | 226° C. |
| 90% vol.: | 285° C. | 270° C. |
| 95% vol.: | 298° C. | 284° C. |
| Final point °C.: | 305° C. | 293° C. |

The distribution by number of carbon atoms, effected by mass spectrometry was as follows for the catalysts FZ1 and FZ2.

| | FZ1 | FZ2 |
|---|---|---|
| C6 | 12.0% | 17.0% |
| C7 | 4.9% | 6.5% |
| C8 | 6.3% | 6.8% |
| C9 | 21.0% | 23.0% |
| C10 | 5.5% | 5.5% |
| C11 | 6.6% | 6.4% |
| C12 | 17.9% | 17.7% |
| C13 | 4.5% | 3.9% |
| C14 | 3.9% | 3.2% |
| C15 | 9.7% | 4.7% |
| C16 | 3.0% | 1.8% |
| C17 | 2.4% | 1.9% |
| C18+ | 2.3% | 1.6% |
| Total | 100 | 100 |

The results obtained show that the ferrizeosilites according to the invention are active in oligomerisation of olefines and that the presence of fluorine coming from the medium of synthesis enables the catalytic performance to be improved.

EXAMPLE 12

Application in catalytic cracking of the ferrizeosilites according to the invention In a first step a zeolite Y is prepared exchanged with rare earths.

50 g of a zeolite NaY in powder form of ratio Si/Al=2.5 were dispersed in a litre of a normal solution of $NH_4NO_3$ and stirred for 1 hour at 100° C. The solid was then filtered, washed then dispersed in a nitrate solution of rare earths (mixture of lanthanum, cerium, neodymium and praseodymium essentially) at pH 5.5 for one hour at 100° C. After a second exchange identical with the preceding one in a fresh solution of rare earth nitrates the zeolite was filtered, washed with distilled water then dried for 4 hours at 150° C. The solid obtained was given the reference REY.

In a second step a ferrizeosilite was prepared according to the method described in Example 5. This ferrizeosilite had a molar ratio $SiO_2/Fe_2O_3$ of 80. Its fluorine content after calcination at 550° C. in air for 9 hours was 0.08% by weight.

In the third step two catalysts A and B were prepared.

The catalyst A contained only zeolite REY. The catalyst B contained a mixture of zeolite REY and ferrizeosilite in the respective proportions of 80 and 20% by weight.

Each catalyst was constituted by 80% by weight of amorphoussilica and 20% by weight of zeolite (REY or mixture of REY+ferrizeosilite). The catalyst B contained therefore 4% by weight of ferrizeosilite. To facilitate the catalytic tests and particularly to limit the charge losses which are associated with the use of powders, each of the constituents (amorphous silica or zeolite) was made into pellets and then crushed, and the fraction of granulometry comprised between 40 and 200 micrometers was recovered by sifting.

The catalysts A and B were tested in the conversion of a distillate under vacuum under the following conditions:
unit in fixed bed
amount of catalyst=4.0 g
ratio by weight catalyst/charge=4.5
WHSV=13.3 h$^{-1}$
reaction time=60 sec. ("time on stream")
reactor temperature=480° C.
charge: density at 15° C.=0.904 aniline point=79° C. % weight S=1.3 % weight N<0.1 % weight C onradson carbon=0.32 Ni+V ppm<1

$$ASTMD\ 1160 \begin{cases} P.I. = 202° \text{ C.} \\ 10\% = 307° \text{ C.} \\ 50\% = 402° \text{ C.} \\ 90\% = 510° \text{ C.} \end{cases}$$

The results obtained were the following:

| | CATALYST A | CATALYST B |
|---|---|---|
| Conversion% | 73.2 | 73.1 |
| Yield gasoline $C_5^+$ % weight | 50.1 | 48.0 |
| Yield gas ($H_2$ + $C_1$ a $C_4$) % | 17.8 | 19.8 |
| coke % | 5.3 | 5.3 |
| Calculated desired octane number (NDR) | 89.3 | 90.9 |
| Propene % | 4.5 | 5.0 |
| Butenes % | 6.1 | 6.9 |
| Potential gasoline (with olefine-isobutane alkylation) | 23.1 | 25.9 |

These results show that the ferrozeosilites contribute a notable gain in octane number of the gasoline (+1.6). The reduction in crude yield of gasoline (−2) which is observed is compensated by an increased production of propene and butenes: with the catalyst B the amount of additional gasoline which can be hoped to recover (potential gasoline) by the alkylation of these olefines with isobutane is infact higher by about 2.8 points than that obtained with catalyst A.

We claim:

1. A synthetic crystalline ferrisilicate zeolite of MFI structure, having:
   (a) the following approximate chemical formula $$M_{2/n}O,\ Fe_2O_3,\ xSiO_2$$

wherein
   M represents a proton and/or a metal cation,
   n is the valence of said cation,
   x is 40 to 1000,
   (b) an x-ray diffraction diagram shown in Table I of the accompanying specification, and
   (c) a fluorine content of about 0.01% to 1.6% weight, wherein the iron is distributed homogeneously within the crystals.

2. A zeolite according to claim 1, comprising crystals of which at least one dimension is about 0.05 to 500 micrometers.

3. A zeolite according to claim 1, wherein the molar ratio $SiO_2/Fe_2O_3$ is 50–750.

4. A catalyst comprising by weight:
   (a) from about 0% to about 99.1% of a matrix selected from the group consisting of alumina, silica, magnesia, zirconia, titanium oxide, boron oxide, a clay, a zeolite other than that of claim 1, and any combination of at least two of the aforesaid compounds, and
   (b) from about 0.1% to about 100% of a zeolite according to claim 1.

5. A process for the preparation of a crystalline synthetic zeolite comprising:
   (a) forming a reaction mixture having a pH less than about 10 comprising water, at least one source of silica, at least one source of ferric salt, at least one source of mobilizing agent containing fluoride ions, at least one source of templating agent which can provide organic cations or a mixture thereof, said reaction mixture having a composition, in terms of molar ratios, of:

| | |
|---|---|
| $SiO_2Fe_2O_3$ | 5–2000 |
| Fluoride/$SiO_2$ | 0.04–4 |
| Organic cations/$SiO_2$ | 0.04–2 |
| $H_2O/SiO_2$ | 6–500. |

(b) keeping said mixture at a temperature at most equal to about 250° C. until a crystalline compound is obtained, and (c) calcining said compound at a temperature above 400° C.

6. A process according to claim 5, wherein the source of templating agent is a source which can provide organic cations selected from the group consisting of tetraalkylammonium, trialkylammonium and tetraalkylphosphonium cations.

7. A process according to claim 5, wherein the source of templating agent is a source which can provide organic cations selected from the group consisting of tetrapropylammonium, tripropylammonium and tetrapropylphosphonium cations.

8. A process according to claim 5, wherein said reaction mixture is prepared at a pH and with a composition in terms of molar ratios of:

| pH | 4–8 |
|---|---|
| $SiO_2/Fe_2O_3$ | 10–1000 |
| Fluoride/$SiO_2$ | 0.1–1.5 |
| Organic cation/$SiO_2$ | 0.08–1 |
| $H_2O/SiO_2$ | 15–350. |

9. A process for the preparation of a crystalline synthetic zeolite according to claim 5, wherein to said reaction mixture is added at least one acid or acid salt to adjust the pH to a value less than 10 at a molar ratio of said acid or acid salt to the silica between about 0.1 and 4 or at least one crystal seed of said zeolite in a ratio by weight of crystal seed to silica between about 0.01 to 0.1.

10. Process according to claim 5, wherein the heating temperature of the reaction mixture is kept between about 60° and 210° C. for a period of about 0.5 to 1100 hours.

11. A zeolite produced by a process comprising:
(a) forming a reaction mixture having a pH less than about 10 comprising water, at least one source of silica, at least one source of ferric salt, at least one source of mobilizing agent containing fluoride ions and/or at least one source of templating agent which can provide organic cations, said mixture having a composition, in terms of molar ratios, comprised within the following ranges of values:

| $SiO_2/Fe_2O_3$ | 5–2000 |
|---|---|
| Fluoride/$SiO_2$ | 0.04–4 |
| Organic cations/$SiO_2$ | 0.04–4 |
| $H_2O/SiO_2$ | 6–500 |

(b) keeping said mixture at a temperature of heating at most equal to about 250° C. until a crystalline compound is obtained, and
(c) calcining said compound at a temperature above 400° C., whereby the resultant zeolite is a ferrisilicate zeolite of MFI structure, having:
 (i) the following approximate chemical formula:

$M_{2/n}O, Fe_2O_3, xSiO_2$ wherein
M represents a proton and/or a metal cation,
n is the valence of said cation,
 (ii) an x-ray diffraction diagram shown in Table I of the accompanying specification, and
 (iii) a fluorine content of about 0.01% to 1.6% by weight.

12. A zeolite according to claim 11 wherein the source of templating agent is a source which can provide organic cations selected from among tetraalkylammonium, trialkylammonium and tetraalkylphosphonium cations.

13. A zeolite according to claim 11 in which the source of templating agent is a source which can provide organic cations selected from among the tetrapropylammonium, tripropylammonium and tetrapropylphosphonium cations.

14. A zeolite according to claim 11 wherein said mixture is prepared at a pH and with a composition in terms of molar ratios comprised within the following ranges of values:

| pH | 4–8 |
|---|---|
| $SiO_2/Fe_2O_3$ | 10–1000 |
| Fluoride/$SiO_2$ | 0.1–1.5 |
| Organic cation/$SiO_2$ | 0.08–1 |
| $H_2O/SiO_2$ | 15–350. |

15. A zeolite according to claim 11 wherein to said mixture is added at least one complementary salt to adjust the pH at a molar ratio of said complementary salt to the silica between about 0.1 and 4 and/or at least one crystal seed of resultant crystalline synthetic zeolite in a ratio by weight of crystal seed silica between about 0.01 and 0.1.

16. A zeolite according to claim 11 wherein the heating temperature of the reaction mixture is kept between about 60° and 210° C. for a period of about 0.5 to 1100 hours.

17. A zeolite produced according to claim 5.

18. A process according to claim 5, wherein the source of silica is reacted with the source of ferric salt to produce a ferrisilicate gel, and the gel is reacted with the agent containing fluoride ions and the source of templating agent.

* * * * *